United States Patent
Cha et al.

(10) Patent No.: US 7,438,690 B2
(45) Date of Patent: Oct. 21, 2008

(54) PEAK EXPIRATORY FLOW METER CAPABLE OF MEASURING CONTINUOUS EXPIRATORY FLOW SIGNAL

(76) Inventors: Eun Jong Cha, Jukong Apt. 208-205, Mochung-Dong, Heugdeok-Gu, Cheongju-City, Chungcheongbuk-Do (KR); Kyung-Ah Kim, 1207 Deokhee Apt. Sajik 2-Dong, Heungdeok-Gu, Cheongju-City, Chungcheongbuk-Do (KR)

( * ) Notice: Subject to any disclaimer, the term of this patent is extended or adjusted under 35 U.S.C. 154(b) by 327 days.

(21) Appl. No.: 10/530,194

(22) PCT Filed: Feb. 20, 2004

(86) PCT No.: PCT/KR2004/000352

§ 371 (c)(1),
(2), (4) Date: Oct. 7, 2005

(87) PCT Pub. No.: WO2004/103175

PCT Pub. Date: Dec. 2, 2004

(65) Prior Publication Data

US 2006/0058698 A1  Mar. 16, 2006

(30) Foreign Application Priority Data

May 23, 2003   (KR)   ...................... 10-2003-0032763

(51) Int. Cl.
*A61B 5/08*   (2006.01)
(52) U.S. Cl. ...................................... 600/538; 600/529

(58) Field of Classification Search ................ 600/484, 600/529, 532, 533, 538, 543
See application file for complete search history.

(56) References Cited

U.S. PATENT DOCUMENTS

| | | | |
|---|---|---|---|
| 5,211,180 A | | 5/1993 | Wright et al. |
| 5,224,487 A | * | 7/1993 | Bellofatto et al. ............ 600/538 |
| 5,540,234 A | * | 7/1996 | Lalui ............................ 600/538 |
| 5,816,246 A | | 10/1998 | Mirza |
| 6,626,845 B2 | * | 9/2003 | Lingo et al. .................. 600/538 |
| 6,626,846 B2 | * | 9/2003 | Spencer ........................ 600/538 |
| 2001/0037071 A1 | | 11/2001 | Lingo, Jr. |
| 2002/0049388 A1 | | 4/2002 | Spencer |

* cited by examiner

*Primary Examiner*—Charles A. Marmor, II
*Assistant Examiner*—Christian Y Jang
(74) *Attorney, Agent, or Firm*—Birch, Stewart, Kolasch & Birch, LLP

(57) ABSTRACT

Disclosed herein is a peak expiratory flow meter capable of measuring continuous expiratory flow. The peak expiratory flow meter includes a lower casing unit (110), an air expansion unit (130) and an upper casing unit (150). The lower casing unit (110) includes a first body (112) having an open top and open opposite sides and having a first end in which a first expiratory flow entrance (114) is formed, a plurality of rails (118), and a movable plate (122). The air expansion unit (130) includes a pressure transfer tube (132), an elastic plate (136), and a pressure spring (140). The upper casing unit (150) includes a second body (152) adapted to define the air expansion unit and provided with a first end in which a second expiratory flow entrance (154) is formed, and a measurement slot (156), and a scale indicator (160) having a "T" shape.

7 Claims, 5 Drawing Sheets

PEAK EXPIRATORY FLOW METER CAPABLE OF MEASURING CONTINUOUS EXPIRATORY FLOW SIGNAL

TECHNICAL FIELD

The present invention relates, in general, to a peak expiratory flow meter being used by asthma patients, and a peak expiratory flow meter, which is capable of measuring continuous expiratory flow.

BACKGROUND ART

Generally, asthma is a chronic respiratory disease, and an asthmatic attack narrowing the respiratory tract is a respiratory disease capable of causing a patient to die (A. Greening, "General principles", In: Manual of asthma management, pp. 331-337, Ed. by P. M. O'byne, N. C. Thomson, W. B. Saunders, New York, 2001). Therefore, an asthma patient must monitor himself or herself, typically performs a forced expiration using a conveniently portable Peak Expiratory Flow Meter (PEFM), and measures Peak Expiratory Flow (PEF) at that time. Typically, the asthma patient recognizes his or her status on the basis of a peak expiratory flow value measured by the PEFM, and then determines whether to go to hospital.

The above-described conventional PEFM is operated on the basis of the principles of FIG. 1, in which one end of a spring 11 having elasticity is fixed to a respiration tube 10 (s) within the respiration tube 10, and the other end thereof is connected to a movable plate 12 movably arranged in the respiration tube 10. Further, an indicator 13 extending through the wall of the expiration tube 10 is arranged to be in contact with the movable plate 12. In FIG. 1, when the expiratory flow F of a patient does not exist, that is, when the PEFM is not used, the movable plate 12 is placed at a location (1) shown in FIG. 1, and the indicator 13 is made to be in close contact with the movable plate 12. When the patient starts to expire, a force of expiratory flow F is applied to the movable plate 12, so that the movable plate 13 starts to move to the right side of the drawing. As a push force obtained by the expiratory flow F increases, a movement distance L is lengthened, and the indicator 13 moves together with the movable plate 12. Simultaneously, the movable plate 12 pulls the spring 11, so that an elastic force is generated and maintained in the spring 11. A patient forcibly expires as in spirometry, which corresponds to a standardized respiratory function examining method of allowing the patient to apply a mouth to the expiration tube 10 and expire as rapidly as possible and as much as possible, after maximally inhaling air. If the value of the push force, generated by the expiratory flow F during the forcible expiration of the patient, starts to decrease from a peak value, the movable plate 12 starts to move to the left side of the drawing due to the elastic force of the spring 11, and consequently returns to (P) its original location (1). However, since the indicator 13, having moved (m) while being in close contact with the movable plate 12, is not connected to the movable plate 12, the indicator 13 moves by the right maximum movement distance L of the movable plate 12 and then remains at a location (2), so that peak expiratory flow is measured by visually measuring the maximum movement distance L.

The above-described peak expiratory flow meter is widely utilized medical instrument, because it allows an asthma patient to conveniently carry and occasionally measure peak expiratory flow if necessary. For the prior arts related to the peak expiratory flow meter, there are patents disclosed in UK Pat. No. 1463814 and U.S. Pat. No. 5,224,487.

The peak expiratory flow meters disclosed in the above prior arts are portable and convenient to use, but they can measure only a peak expiratory flow value in a spirometry process executed while a patient forcibly expires. However, typically, the evaluation of the respiratory function of a chronic respiratory disease patient, such as an asthma patient, is possible only when an expiratory flow signal is continuously measured during the forcible expiration and then important index values, such as Forced Vital Capacity (FVC) and Forced Expiratory Volume at 1 sec ($FEV_{1.0}$), are obtained together from the measured signal waveform (R. E. Kanner, and A. H. Morris, "Forced expiratory spirogram", In: Clinical pulmonary function testing, pp. I-7~10, Intermountain Thoracic Society, Salt Lake City, 1975). However, the above-described conventional peak expiratory flow meters are limited in the evaluation of the respiratory function because they provide only a peak expiratory flow value, which is the maximum value of the expiratory flow.

Further, when FVC, $FEV_{1.0}$ and PEF, which are important and essential indexes to evaluate the respiratory function, are required to be simultaneously obtained, an expensive spirometer must be used, which has a construction completely different from that of the PEFM in an entire operating structure including the principles of measurement of an expiratory flow signal. Therefore, when an asthma patient desires to currently evaluate the respiratory function thereof, there is a problem in that he or she must measure only a PEF value using the PEFM, or utilize a separate spirometer.

DISCLOSURE OF THE INVENTION

Accordingly, the present invention has been made keeping in mind the above problems occurring in the prior art, and an object of the present invention is to provide a peak expiratory flow meter capable of measuring continuous expiratory flow, which improves the construction of a peak expiratory flow meter having a miniatured air expansion chamber therein to obtain a pressure signal corresponding to a continuous flow signal through the peak expiratory flow meter, so that an actual spirometer function is provided, thus enabling the present invention to be used as a typical peak expiratory flow meter at ordinary times, and allowing a signal accumulation and analysis circuit to be connected to the peak expiratory flow meter to execute spirometry if necessary.

BEST MODE FOR CARRYING OUT THE INVENTION

The present invention provides a peak expiratory flow meter capable of measuring continuous expiratory flow, comprising a lower casing unit including a first body formed to have an open top and open opposite sides and to have a first end in which a first expiratory flow entrance is formed to be integrated with the first body so as to allow an asthma patient to hold the first expiratory flow entrance in his or her mouth, a plurality of rails arranged on a top of the first body adjacent to a second end of the first body, and a movable plate fitted on the rails; an air expansion unit including a pressure transfer tube arranged on a side of the first expiratory flow entrance, an elastic plate fitted on the pressure transfer tube, and a pressure spring comprised of a first end that is mounted to the elastic plate and a second end that is mounted on a first side surface of the movable plate; and an upper casing unit including a second body coupled with the first body, adapted to define the air expansion unit and provided with a first end in which a second expiratory flow entrance corresponding to the first expiratory flow entrance is formed to be integrated with the second body, and a measurement slot formed on a side of the second expiratory flow entrance and extended to a portion of the second body adjacent to a second end of the second body, and a scale indicator formed to have a "T" shape and to have an upper portion exposed to outside of the measurement slot, and hung on a top of the second body and a lower portion supported on an upper portion of a second side surface of the movable plate, the scale indicator being moved by the movable plate.

As described above, the present invention is advantageous in that it improves the construction of a peak expiratory flow meter having a miniatured air expansion chamber therein to obtain a pressure signal corresponding to a continuous flow signal through the peak expiratory flow meter, so that an actual spirometer function is provided, thus enabling the present invention to be used as a typical peak expiratory flow meter at ordinary times, and allowing a signal accumulation and analysis circuit to be connected to the peak expiratory flow meter to execute spirometry if necessary.

Hereinafter, embodiments of the present invention will be described in detail with reference to the attached drawings.

Figure 1:
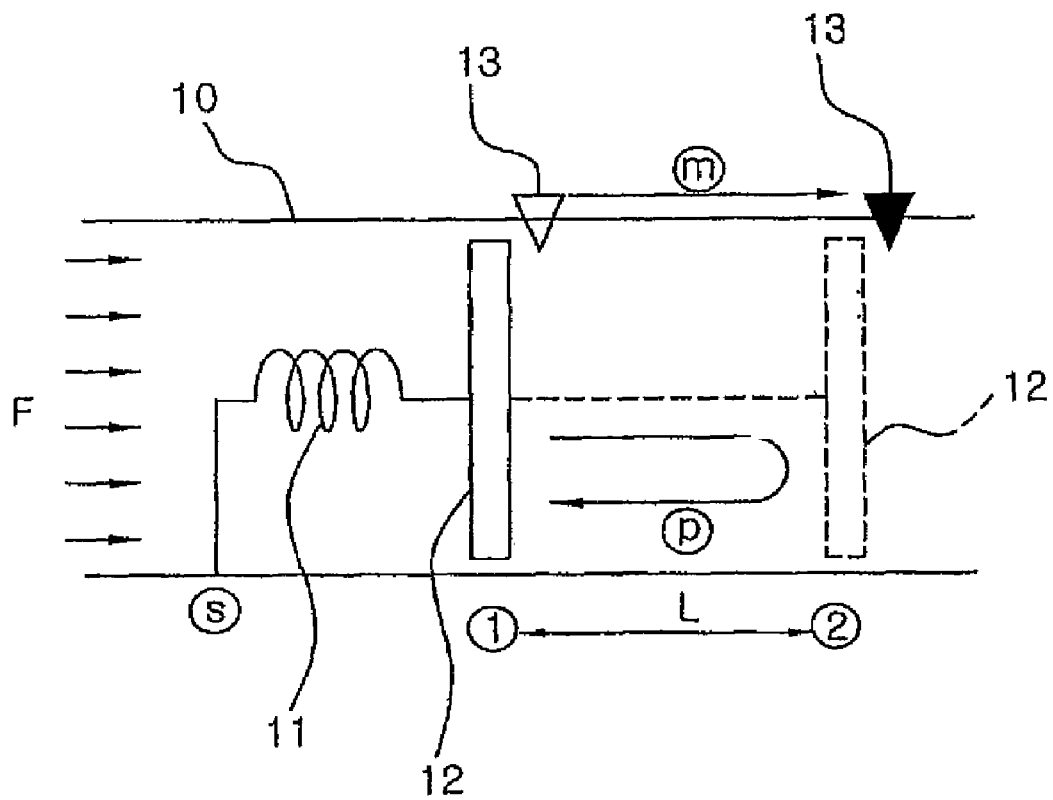
FIG. 1 is a view schematically showing the operating principles of a conventional peak expiratory flow meter.
Figure 2:
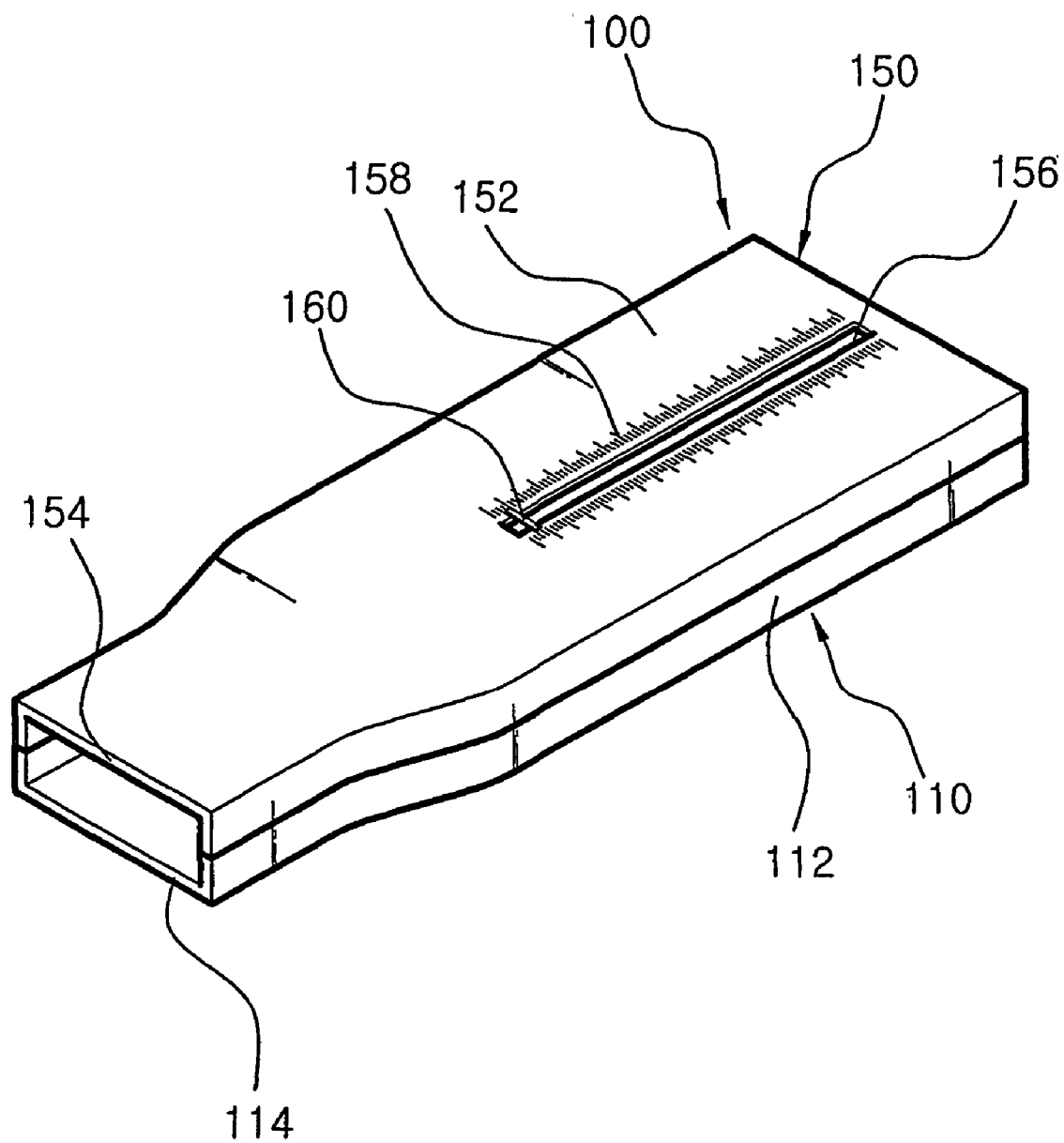
FIG. 2 is a perspective view showing the coupling state of a peak expiratory flow meter capable of measuring continuous expiratory flow according to the present invention.
Figure 3:
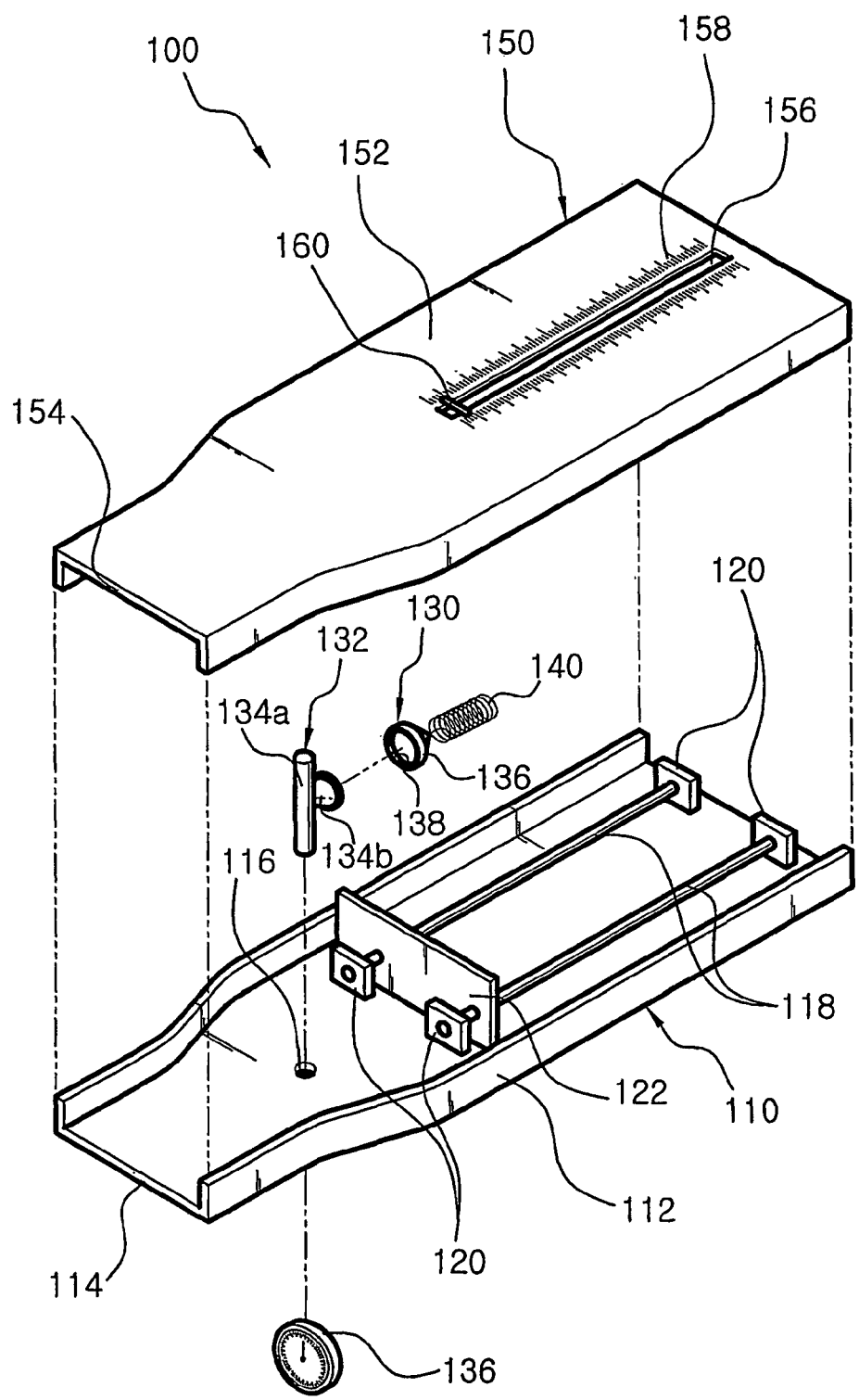
FIG. 3 is an exploded perspective view of the peak expiratory flow meter of FIG. 2.
Figure 4:
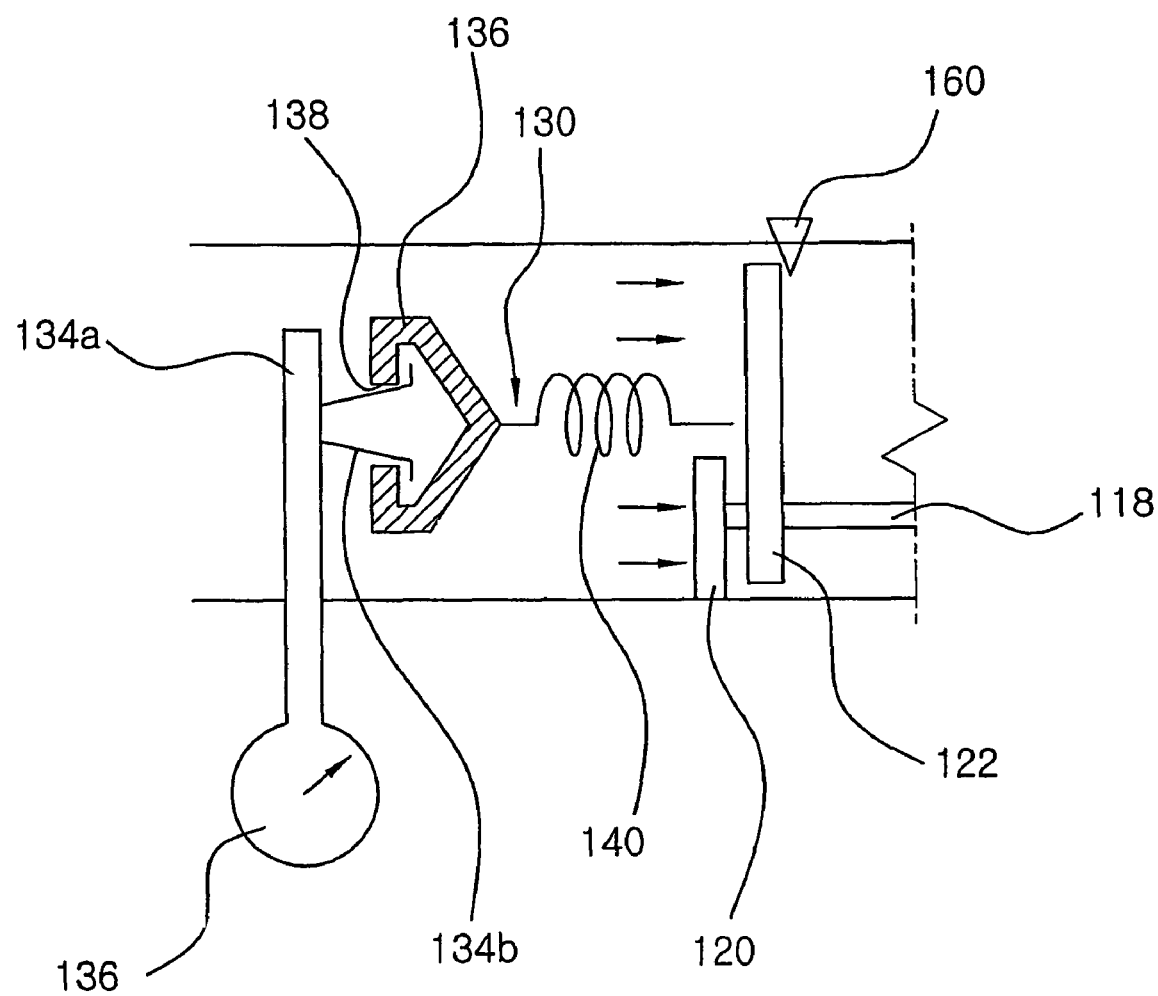
FIG. 4 is a view schematically showing the operating principles of the peak expiratory flow meter according to the present invention.

FIG. 2 is a perspective view showing the coupling state of a peak expiratory flow meter capable of measuring continuous expiratory flow according to the present invention, and FIG. 3 is an exploded perspective view of the peak expiratory flow meter of FIG. 2.

Referring to FIGS. 2 and 3, a peak expiratory flow meter 100 capable of measuring continuous expiratory flow according to the present invention includes a lower casing unit 110, an air expansion unit 130, and an upper casing unit 150.

First, the lower casing unit 110 includes a first body 112 and rails 118. The first body 112 is formed to have an open top and open opposite sides. A first expiratory flow entrance 114, which radially narrows to allow an asthma patient to hold the entrance 114 in his or her mouth, is formed at one end of the first body 112 to be integrated with the first body 112. A pressure transfer hole 116 penetrating through the bottom surface of the first body 112 is formed on a side of the first expiratory flow entrance 114. In the meantime, the rails 118 are arranged on the top surface of the first body 112 adjacent to the other end of the first body 112. Such rails 118 are arranged to be spaced apart from each other by a certain distance around the pressure transfer hole 116, and extended to the other end of the first body 112, respectively. The ends of the respective rails 118 are fixedly arranged by supporting projections 120 vertically extended from the bottom surface of the first body 112. A movable plate 122 having a vertical planar shape is slidably fitted on the rails 118. The air expansion unit 130 and the upper casing unit 150 are mounted on the lower casing unit 110 formed as described above.

The air expansion unit 130 includes a pressure transfer tube 132 and an elastic plate 136. The pressure transfer tube 132 includes a first transfer tube 134a and a second transfer tube 134b. The first transfer tube 134a is extended from the top of the body 112 to the outside of the first body 112 through the pressure transfer hole 116. At this time, the top of the first transfer tube 134a is closed, and the bottom thereof is opened to allow any one of a typical pressure sensor 136 and an electronic circuit for signal analysis to be selectively mounted on the bottom. The second transfer tube 134b is extended from the outer circumference of the first transfer tube 134a, arranged inside of the first body 112, to the movable plate 122 so that the second transfer plate 134b is radially broadened. That is, the second and first transfer tubes 134b and 134a communicate with each other. The elastic plate 136 may be formed to have a vertically arranged disk shape. A mounting cavity 138 is formed in a portion of one side surface of the elastic plate 136 so that the extending part of the second transfer tube 134b can be fitted into the cavity 138, and one end of a pressure spring 140 is mounted on the other side surface of the elastic plate 136. At this time, the other end of the pressure spring 140 is mounted on one side surface of the movable plate 122.

In the meantime, the upper casing unit 150 includes a second body 152 and a scale indicator 160. The second body 152 is formed to have an open bottom and open sides to be coupled with the first body 112. A second expiratory flow entrance 154 corresponding to the first expiratory flow entrance 114 is formed at one end of the second body 152. A measurement slot 156 extending to a portion of the second body 152 adjacent to the other end of the second body 152 is formed on a side of the second expiratory flow entrance 154 to penetrate through the top of the second body 152. In this case, a scale 158 is indicated to both sides of the measurement slot 156. The scale indicator 160 is formed in an approximate "T" shape. The upper portion of the scale indicator 160 is exposed to the outside of the measurement slot 156 and hung on the top of the second body 152, and the lower portion thereof is supported on the upper portion of the other side surface of the movable plate 122. That is, the scale indicator 160 moves with the movable plate 122, and the air expansion unit 130 arranged in the first body 112 is defined to be between the first and second bodies 112 and 152 by the second body 150.

Hereinafter, the operating state of the peak expiratory flow meter 100 formed as described above is described briefly.

First, the air expansion unit 130 is mounted on the lower casing unit 110 having the first body 112 in which the movable plate 122 is slidably fitted on the rails 118. In this case, the first and second transfer tubes 134a and 134b of the pressure transfer tube 132 of the air expansion unit 130 are fitted into the pressure transfer hole 116, and the mounting cavity 138 of the elastic plate 136, respectively. In this case, the first transfer tube 134a and the second transfer tube 134b are tightly fitted into the pressure transfer hole 116 and the mounting cavity 138, respectively, to prevent the circulation of air therebetween. The other end of the pressure spring 140 mounted on the elastic plate 136 is mounted to one side surface of the movable plate 122.

As described above, when the air expansion unit 130 is mounted on the lower casing unit 110, the upper casing unit 150 having the second body 152, in which the scale indicator 160 is installed, covers the top of the lower casing unit 110, thus closing the top of the lower casing unit 110. At this time, the lower portion of the scale indicator 160 is arranged to be in close contact with the other side surface of the movable plate 122, thus enabling the scale indicator 160 to react to the movement of the movable plate 122.

In the peak expiratory flow meter 100 formed as described above, when the expiratory flow F passing into the flow meter 100 through the first and second expiratory flow entrances 114 and 154 pushes the movable plate 122 to stretch the pressure spring 140, an elastic force is generated in the pressure spring 140 to pull the elastic plate 136, so that the expansion of air occurs in both the elastic plate 136 and the pressure transfer tube 132, thus forming a vacuum pressure, that is, a negative pressure. Further, the movement distance of the movable plate 122 varies with the level of the expiratory flow F, and the elastic force varies in proportion to the movement distance, so that the pressure P formed in the air expansion unit 130 is proportional to the expiratory flow F and reflects the continuous variations of the expiratory flow F, and the pressure spring 140 is fixedly connected to the air expansion unit 130 reacting to the pressure spring 140, thus obtaining a pressure signal proportional to the expiratory flow F.

Further, in the peak expiratory flow meter 100, the movable plate 122 can safely move along the plurality of symmetrically arranged rails 118. If the expiratory flow F flows from the first and second expiratory flow entrances 114 and 154, the movable plate 122 is moved, and the elastic plate 136 is pulled together as the pressure spring 140 is pulled, so that the negative pressure proportional to the expiratory flow F is formed. In the meantime, the negative pressure is continuously measured by the pressure sensor 136 connected to the outside of the flow meter 100 through the pressure transfer tube 132, so that a flow signal can be continuously measured during the forcible expiration of the patient.

Moreover, with respect to the present invention as described above, the characteristics of pressure and expiratory flow were calculated using the mechanism and method proposed in Korean Pat. Appl. No. 2002-1151 filed by the present applicant.

Figure 5:
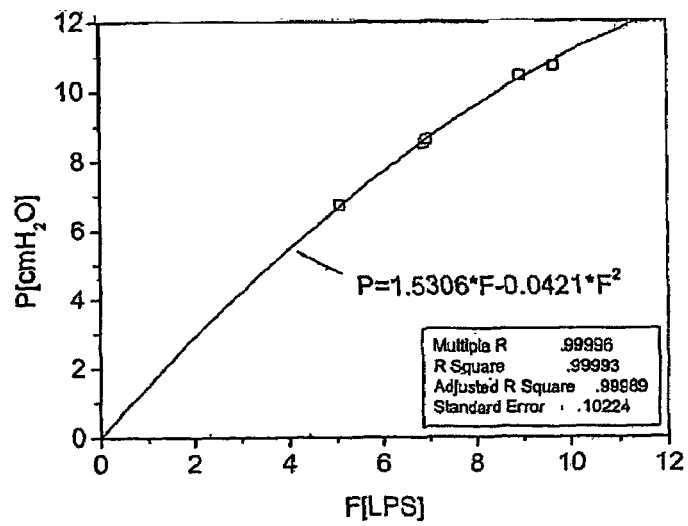
FIG. 5 is a graph showing the characteristics of pressure and flow.
Figure 6:
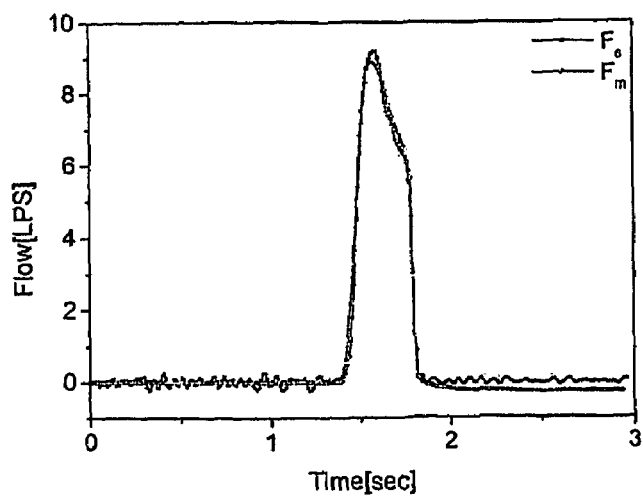
FIG. 6 is a graph showing an example of the comparison of standard flow with measured flow.

FIG. 5 is a graph showing the characteristics of pressure P and expiratory flow F obtained through stroke experiments carried out six times. A mathematical formula between the pressure P and the expiratory flow F can be almost exactly expressed in the form of a quadratic function (correlation coefficient=0.99996). The reason that the pressure P and the expiratory flow F are not simply proportional to each other is due to the fact that the operation of a mechanism using a frictional force and inertia is not ideal, so the formula deviates from a theoretical proportional relationship. However, if the solution of a quadratic equation is obtained after the pressure P is measured, the expiratory flow F is obtained, and then it can be seen that there is no practical problem. For example, the pressure P is continuously measured to obtain the expiratory flow F (measured flow: Fm), which is compared to a standard flow signal (standard flow: Fs), which is actually applied, so that the comparison results therebetween are shown in FIG. 6. In this case, it can be seen that Fm and Fs are almost equal to each other, which experimentally proves the usefulness of the peak expiratory flow meter 100 capable of measuring continuous expiratory flow according to the present invention.

INDUSTRIAL APPLICABILITY

As described above, the peak expiratory flow meter 100 capable of measuring continuous expiratory flow according to the present invention is advantageous in that a movable plate 122 for moving a scale indicator 160 is fitted on a plurality of rails 118, thus enabling the scale indicator 160 to exactly move without being shaken.

Further, the present invention is advantageous in that, since any one of a pressure sensor 136 and an electronic circuit (not shown) is mounted to a first transfer tube 134a of a pressure transfer tube 132, spirometry can be performed using a suitable method, so that the peak expiratory flow meter 100 has excellent flexibility and is manufactured at low cost, thus increasing a customer's desire to purchase the peak expiratory flow meter 100.

Although the preferred embodiment of the present invention has been disclosed for illustrative purposes, those skilled in the art will appreciate that various modifications, additions and substitutions are possible, without departing from the scope and spirit of the invention as disclosed in the accompanying claims.

The invention claimed is:

1. A peak expiratory flow meter capable of measuring continuous expiratory flow, comprising:

a lower casing unit including a first body formed to have an open top and open opposite sides and to have a first end in which a first expiratory flow entrance is formed to be integrated with the first body so as to allow an asthma patient to hold the first expiratory flow entrance in his or her mouth, a plurality of rails arranged on a top of the first body adjacent to a second end of the first body, and a movable plate fitted on the rails;

an air expansion unit including a pressure transfer tube arranged on a side of the first expiratory flow entrance, an elastic plate fitted on the pressure transfer tube, and a pressure spring comprised of a first end that is mounted to the elastic plate and a second end that is mounted on a first side surface of the movable plate; and an upper casing unit including a second body coupled with the first body, adapted to define the air expansion unit and provided with a first end in which a second expiratory flow entrance corresponding to the first expiratory flow entrance is formed to be integrated with the second body, and a measurement slot formed on a side of the second expiratory flow entrance and extended to a portion of the second body adjacent to a second end of the second body, and a scale indicator formed to have a "T" shape and to have an upper portion exposed to outside of the measurement slot and hung on a top of the second body and a lower portion supported on an upper portion of a second side surface of the movable plate, the scale indicator being moved by the movable plate.

2. The peak expiratory flow meter according to claim 1, wherein the rails have ends that are fixedly arranged by supporting projections vertically extended from a bottom surface of the first body.

3. The peak expiratory flow meter according to claim 1, wherein the lower casing unit has a pressure transfer hole that is formed on a side thereof to penetrate through a bottom surface of the first body.

4. The peak expiratory flow meter according to claim 3, wherein the pressure transfer tube includes a first transfer tube that is formed to have a closed top and an open bottom to penetrate from the top of the first body through the pressure transfer hole, and a second transfer tube that is extended from an outer circumference of the first transfer tube, arranged in the first body, to be radially broadened towards the movable plate while communicating with the first transfer tube, and then mounted to the elastic plate, the pressure transfer hole being tightly fitted around the first transfer tube, which passes therethrough, without circulation of air therebetween.

5. The peak expiratory flow meter according to claim 4, wherein the first transfer tube extended to an outside of the first body is selectively connected to any one of a typical pressure sensor and a typical electronic circuit for signal analysis, thus performing spirometry.

6. The peak expiratory flow meter according to claim 4, wherein the elastic plate includes a mounting cavity that is formed in a portion thereof to allow an extending part of the second transfer tube to be fitted into the mounting cavity, the second transfer tube being tightly fitted into the mounting cavity without circulation of air therebetween.

7. The peak expiratory flow meter according to claim 1, wherein the measurement slot is formed to penetrate through the top of the second body, the second body having a scale indicated to both sides of the measurement slot.

* * * * *